US00RE38170E

(19) United States
(12) Reissued Patent
DeGeorge et al.

(10) Patent Number: US RE38,170 E
(45) Date of Reissued Patent: Jul. 1, 2003

(54) GAS CONVERSION USING SYNTHESIS GAS PRODUCED HYDROGEN FOR CATALYST REJUVENATION AND HYDROCARBON CONVERSION

(75) Inventors: Charles William DeGeorge, Vienna, VA (US); Robert Dean Denton, Bellaire, TX (US)

(73) Assignee: ExxonMobil Research and Engineering Company, Annandale, NJ (US)

(21) Appl. No.: 10/109,621

(22) Filed: Mar. 28, 2002

Related U.S. Patent Documents

Reissue of:
(64) Patent No.: 6,043,288
Issued: Mar. 28, 2000
Appl. No.: 09/023,581
Filed: Feb. 13, 1998

(51) Int. Cl.[7] ..... C07C 27/00; C07C 27/06; C07C 1/02; C10G 45/00; C10G 65/00

(52) U.S. Cl. ..... 518/715; 518/702; 518/709; 518/700; 518/722; 252/373; 208/56; 208/59

(58) Field of Search ..... 518/702, 709, 518/715, 722, 700; 252/373; 208/56, 59

(56) References Cited

U.S. PATENT DOCUMENTS 2,251,554 A * 8/1941 Sabel et al. ..... 260/449
2,609,382 A * 9/1952 Mayland ..... 260/449.6
3,890,113 A * 6/1975 Child et al. ..... 48/197 R
4,049,741 A * 9/1977 Kuo et al. ..... 260/676 R
5,260,239 A * 11/1993 Hsia ..... 502/30
5,283,216 A * 2/1994 Mitchell
5,322,617 A * 6/1994 de Bruijn et al. ..... 208/108
5,844,005 A * 12/1998 Bauman et al. ..... 518/700

FOREIGN PATENT DOCUMENTS

EP 0269297 A1 * 6/1988 ..... C07C/15/00
EP 0400743 * 5/1990 ..... C10G/47/00
EP 0512635 A2 * 11/1992 ..... C07C/1/08
EP 0583836 * 5/1993 ..... C10G/65/12
GB 2299767 * 10/1996 ..... B01J/23/90
NL 8102071 * 12/1981 ..... C10G/1/04

OTHER PUBLICATIONS

D. M. Bibby, et al. (eds), SYNGAS FOR $C_1$—CHEMISTRY.*
Limits of the Steam Reforming Process, Methane Conversion, pp. 73–78, (Elsevierm, 1988).*

* cited by examiner

*Primary Examiner*—J. Parsa
(74) *Attorney, Agent, or Firm*—Mark D. Marin

(57) ABSTRACT

A gas conversion process in which both hydrocarbons and hydrogen are produced from a synthesis gas feed which comprises a mixture of $H_2$ and CO, uses hydrogen from a portion of the feed for one or more of (i) hydrocarbon synthesis catalyst rejuvenation and (ii) hydroconversion upgrading of at least a portion of the synthesized hydrocarbons. Hydrogen is produced from a slipstream of the synthesis gas fed into the hydrocarbon synthesis reactor by one or more of (i) physical separation means such as pressure swing adsorption and (ii) chemical means such as a water gas shift reactor. If a shift reactor is used due to insufficient capacity of the synthesis gas generator, physical separation means such as pressure swing adsorption will still be used to separate a pure stream of hydrogen from the shift reactor gas effluent.

18 Claims, 2 Drawing Sheets

GAS CONVERSION USING SYNTHESIS GAS PRODUCED HYDROGEN FOR CATALYST REJUVENATION AND HYDROCARBON CONVERSION

Matter enclosed in heavy brackets [ ] appears in the original patent but forms no part of this reissue specification; matter printed in italics indicates the additions made by reissue.

BACKGROUND OF THE DISCLOSURE

1. Field of the Invention

The invention relates to a process in which both hydrocarbons and hydrogen are produced from syngas. More particularly, the invention relates to a gas conversion process for synthesizing hydrocarbons and producing hydrogen from syngas, with the hydrogen used for at least one of (i) hydrocarbon synthesis catalyst rejuvenation and (ii) hydrocarbon product upgrading.

2. Background of the Invention

Hydrocarbon synthesis processes are known in which a synthesis gas feed comprising a mixture of $H_2$ and CO is fed into a hydrocarbon synthesis reactor in which it reacts in the presence of a Fischer-Tropsch catalyst under conditions effective to form higher molecular weight hydrocarbons. These processes include fixed bed, fluid bed and slurry hydrocarbon synthesis, all of which are well documented in various technical articles and in patents. In many cases it is desired that the synthesized hydrocarbons comprise mostly $C_{5+}$ hydrocarbons (e.g., $C_{5+}$–$C_{200}$) and preferably $C_{10+}$ hydrocarbons, at least a portion of which are solid at standard conditions of room temperature and pressure. It is preferred in a slurry hydrocarbon synthesis process that the hydrocarbons comprise mostly $C_{5+}$ paraffins. These hydrocarbons are upgraded to more valuable products by one or more hydroconversion operations in which at least a portion of the molecular structure is changed by reacting with hydrogen. Hydroconversion operations therefore all require hydrogen. Hydrogen is also required for rejuvenating the hydrocarbon synthesis catalyst and sometimes for maintaining or changing the $H_2$ to CO ratio of the syngas feed for the hydrocarbon synthesis. It is desirable to have a hydrocarbon synthesis process which generates the hydrogen required for the hydrocarbon synthesis catalyst rejuvenation and also for the hydroconversion upgrading of the synthesized hydrocarbons, rather than depending on an outside source of hydrogen.

SUMMARY OF THE INVENTION

The present invention relates to a gas conversion process for catalytically synthesizing hydrocarbons and producing hydrogen from a synthesis gas (syngas) comprising a mixture of $H_2$ and CO, and upgrading the synthesized hydrocarbons, wherein the hydrogen is used for at least one of (a) hydrocarbon synthesis catalyst rejuvenation and (b) upgrading at least a portion of the synthesized hydrocarbons by at least one hydroconversion operation. By gas conversion process is meant to include at least hydrocarbon synthesis and hydrogen production from syngas, and also conversion of at least a portion of the synthesized hydrocarbons. By conversion is meant a process in which the molecular structure of at least a portion of the hydrocarbon in a conversion zone is changed and includes both catalytic and non-catalytic processes, with or without hydrogen as a coreactant as is explained below. In a broad sense therefore, the invention comprises synthesizing hydrocarbons and producing hydrogen from a syngas, and using the syngas produced hydrogen for at least one of the processes set forth above. More specifically, the invention comprises a gas conversion process including hydrocarbon synthesis and hydrogen production from synthesis gas comprising a mixture of $H_2$ and CO, and conversion of at least a portion of said synthesized hydrocarbons, said process comprising contacting said synthesis gas with a hydrocarbon synthesis catalyst, reacting said $H_2$ and CO in the presence of said synthesis catalyst and species which reversibly deactivate said catalyst, at reaction conditions effective to form hydrocarbons and reversibly deactivate said catalyst, upgrading at least a portion of said synthesized hydrocarbons by at least one conversion operation, and at least one of (a) rejuvenating said catalyst by contacting it with said hydrogen produced from said syngas and (b) upgrading at least a portion of said hydrocarbons by reacting them with said hydrogen produced from said syngas in the presence of a hydroconversion catalyst to alter their molecular structure. In further embodiments, the hydrogen produced from the syngas may be used for the hydrocarbon synthesis and/or the hydrogen production. The hydrogen is produced from the syngas using one or more of (a) physical separation means such as pressure swing adsorption (PSA), membrane separation or thermal swing adsorption (TSA), and (b) chemical means such as a water gas shift reaction. Physical means for the hydrogen production will typically be used to separate the hydrogen from the syngas, irrespective of whether or not chemical means such as a water gas shift reaction is used. In order to obtain hydrogen of the desired degree of purity (e.g., at least about 99%). While it is possible that the syngas will be obtained from an outside source, typically the syngas formation will also be a part of the gas conversion process. Thus, in an embodiment in which the syngas production is part of the gas conversion plant, the invention comprises (a) reacting a gaseous hydrocarbonaceous material, oxygen and optionally steam at conditions effective to form a syngas comprising a mixture of $H_2$ and CO, (b) contacting a portion of said syngas with a hydrocarbon synthesis catalyst at reaction conditions effective to react said $H_2$ and CO and form hydrocarbons and reversibly deactivate said catalyst, (c) producing hydrogen from another portion of said syngas, and (d) using the hydrogen for at least one of (i) rejuvenating said catalyst and (ii) hydroconverting at least a portion of said synthesized hydrocarbons.

The hydrocarbon synthesis is accomplished by reacting the syngas in an HCS reaction zone or reactor, in the presence of a Fischer-Tropsch catalyst, at conditions effective to form hydrocarbons and preferably $C_{5+}$ hydrocarbons. As is known, during the HCS reaction, the HCS catalyst reversibly deactivates due to the presence of catalyst deactivating species, such as nitrogen compounds present in the syngas (e.g., HCN and $NH_3$) and possibly others formed by the HCS reaction. It is also known that the catalytic activity is restored (rejuvenated) by contacting the catalyst with hydrogen or a gas comprising hydrogen. At least a portion of the synthesized hydrocarbon product removed from the HCS reactor is upgraded by at least one conversion operation, to reduce its viscosity or pour point, or to convert them into boiling fractions of higher value. Typically the conversion will comprise at least one hydroconversion operation in which the hydrocarbons react with hydrogen in the presence of a hydroconversion catalyst. It is preferred that a gas conversion plant provide at least a portion of the hydrogen needed for one or more of these uses within the plant, rather than be dependent on an outside source.

Producing hydrogen from the syngas using physical separation means provides relatively pure hydrogen, along with an offgas which comprises a hydrogen depleted and CO rich mixture of $H_2$ and CO. This CO rich offgas may be used as fuel or fed into the HCS reaction zone. If the demand for hydrogen is greater than can be met by separating hydrogen from the syngas, or if an ancillary or alternate means for producing hydrogen is desired, chemical means such as a water gas shift reactor may be used to produce, from the syngas, all or a portion of the hydrogen required. In this embodiment, at least one of (a) a portion of the syngas and (b) the CO rich offgas resulting from physically separating hydrogen from the syngas, are fed into a water gas shift reactor in the presence of steam and a water gas shift catalyst to form a mixture of $H_2$ and $CO_2$ from the CO and steam, which is then passed through physical separation means to separate the $H_2$ from the rest of the gas and form relatively pure $H_2$, and a CO rich offgas, with the offgas recycled back into either the HCS reaction zone, into the shift reactor, or used as fuel.

DETAILED DESCRIPTION

Figure 1:
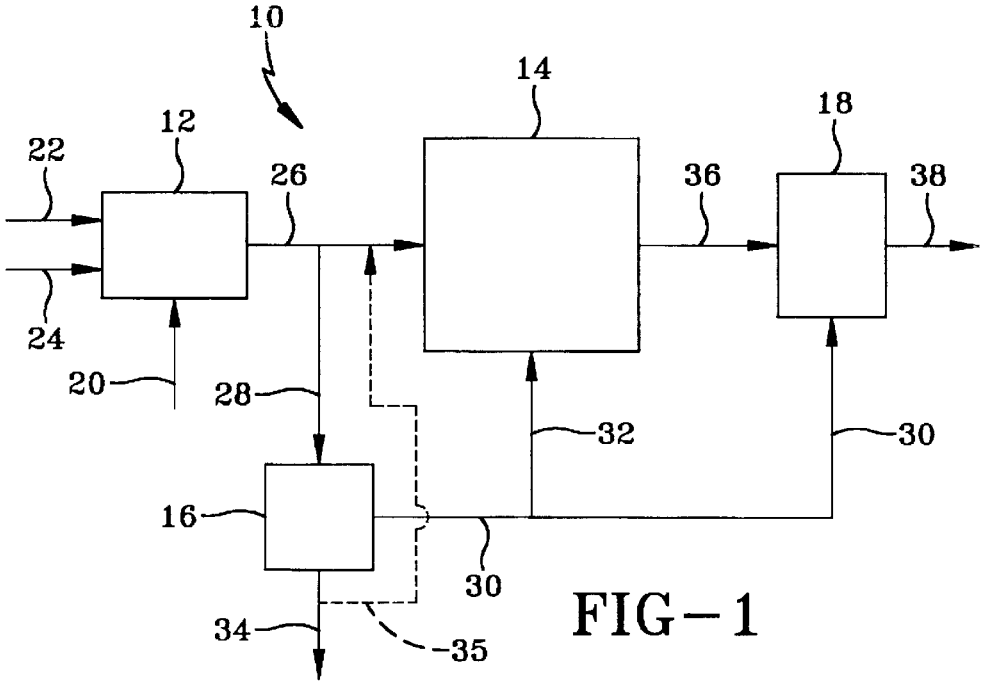
FIG. 1 is a simple block flow diagram of one embodiment of the invention in which hydrogen produced from syngas is used for catalyst rejuvenation and hydroconversion.

The hydrocarbon component of the feed for the syngas generation, while conveniently derived from natural gas which comprises mostly methane as the hydrocarbon component, may be obtained by any available and convenient means from any suitable hydrocarbonaceous material, including coal, coke, hydrocarbon liquids and gas, as is well known. Typically a plant for synthesizing hydrocarbons will be proximate a source of such hydrocarbonaceous materials and the syngas generating operation will be an integral part of the plant. Feeds comprising a low molecular weight (e.g., $C_1$–$C_4$) hydrocarbon, preferably alkane and more preferably mostly methane, as in natural gas, are preferred. Natural gas is particularly preferred because it comprises primarily methane, is convenient, clean and doesn't leave large quantities of ash, shale, sulfur compounds and the like to be handled and disposed of. The syngas may be formed by various means, including contacting a hot carbonaceous material, such as coal, coke or tar, with steam and from burning such material under partial oxidation conditions to form methane or a low molecular weight hydrocarbon gas as the hydrocarbon component of feed to a syngas generator, which is then fed into the syngas generator in which it is partially oxidized with oxygen or air and either steam reformed or passed into a water gas shift reactor. Partial oxidation and steam reforming is accomplished with the steam reforming catalyst in either a fixed or fluid bed, with a fluid bed having superior mixing and heat transfer characteristics. In catalytic partial oxidation, the hydrocarbon component of the feed to the syngas generator is premixed with oxygen, and optionally steam, and passed into the syngas generator in which it reacts in the presence of a noble metal catalyst and preferably a supported noble metal catalyst as is known. These processes use a low molecular weight hydrocarbon, typically a $C_1$–$C_4$ alkane, and preferably methane as in natural gas which, along with steam, oxygen or air is fed into the syngas generating unit. In a fluid bed syngas generating (FBSG) process, the partial oxidation and steam reforming both occur in the presence of the steam reforming catalyst. FBSG is disclosed, for example, in U.S. Pat. Nos. 4,888,131 and 5,160,456. In autothermal reforming, partial oxidation occurs in the absence of a catalyst and precedes adiabatic steam reforming which occurs in a fixed bed of catalyst. The syngas exiting the reactor comprises a mixture of $H_2$ and CO along with water vapor or steam, nitrogen, $CO_2$ and minor amounts of unreacted methane. The amount of $CO_2$ present in the feed to the syngas generator will effect the reaction equilibrium and may be used, along with the conditions in the unit, to adjust the $H_2$ to CO ratio of the syngas. Most of the water is removed from the syngas before it is passed into an HCS reactor. Irrespective of either the source of the hydrocarbon for the syngas production or the process, such hydrocarbon feeds invariably contain elemental nitrogen or nitrogen containing compounds which react in the syngas generator to form nitrogenous species, such as HCN and $NH_3$, which deactivate the HCS catalyst during the HCS reaction.

In an HCS process, liquid and gaseous hydrocarbon products are formed by contacting a syngas comprising a mixture of $H_2$ and CO with a Fischer-Tropsch type of HCS catalyst, under shifting or non-shifting conditions and preferably under non-shifting conditions in which little or no water gas shift reaction occurs, particularly when the catalytic metal comprises Co, Ru or mixture thereof Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

With respect to the hydrocarbon synthesis, fixed bed, fluid bed and slurry hydrocarbon synthesis (HCS) processes for forming hydrocarbons from a syngas comprising a mixture of $H_2$ and CO are well known and documented in the literature. In all of these processes the syngas is reacted in the presence of a suitable Fischer-Tropsch type of hydrocarbon synthesis catalyst, at reaction conditions effective to form hydrocarbons. Some of these hydrocarbons will be liquid, some solid (e.g., wax) and some gas at standard room temperature conditions of temperature and pressure of 25° C. and one atmosphere, particularly if a catalyst having a catalytic cobalt component is used. Slurry HCS processes are often preferred because of their superior heat (and mass) transfer characteristics for the strongly exothermic synthesis reaction and because they are able to produce relatively high molecular weight, paraffinic hydrocarbons when using a cobalt catalyst. In a slurry HCS process a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide may broadly range from about 0.5 to 4, but is more typically within the range of from about 0.7 to 2.75 and preferably from about 0.7 to 2.5. The stoichiometric mole ratio for a Fischer-Tropsch HCS reaction is 2.0, but in the practice of the present invention it may be increased to obtain the amount of hydrogen desired from the syngas for other than the HCS reaction. In a slurry HCS process the mole ratio of the $H_2$ to CO is typically about 2.1/1. Slurry HCS process conditions vary somewhat depending on the catalyst and desired products. Typical conditions effective to form hydrocarbons comprising mostly $C_{5+}$ paraffins, (e.g., $C_{5+}$–$C_{200}$) and preferably $C_{10+}$ paraffins, in a slurry HCS process employing a catalyst comprising a supported cobalt component include, for example, temperatures, pressures and hourly gas space velocities in the range of from about 320–600° F., 80–600 psi and 100–40,000 V/hr/V, expressed as standard volumes of the gaseous CO and $H_2$ mixture (0° C., 1 atm) per hour per volume of catalyst, respectively. During the hydrocarbon synthesis operation, the HCS catalyst loses activity (deactivates) by deactivating species mentioned above present in the syngas and resulting from the synthesis reaction. This deactivation is reversible and catalytic activity is restored (the catalyst rejuvenated) by contacting the deactivated catalyst with hydrogen. The activity of the HCS catalyst in the reactive slurry is intermittently or continuously rejuvenated by contacting the slurry with hydrogen or a hydrogen containing gas to form a catalyst rejuvenated slurry either in-situ in the HCS reactor or in an external rejuvenation vessel, as is disclosed, for example, in U.S. Pat. Nos. 5,260,239; 5,268,344, and 5,283,216.

Physical separation processes useful for producing hydrogen from the syngas include adsorption-desorption processes and membrane separation, both of which are well known and commercially available. Adsorption-desorption processes include TSA and PSA, both of which comprise a plurality of adsorbent containing vessels operated in a cyclic manner. Adsorbents include molecular sieves, silica gel and activated carbon. The difference between pressure swing adsorption and thermal swing adsorption, is that the gas constituents other than hydrogen which are primarily adsorbed by the adsorbent during the adsorption part of the cycle are desorbed from the adsorbent during regeneration by a pressure swing cycle in PSA, as opposed to a thermal swing cycle in thermal swing adsorption. The pressure differential between adsorption and desorption is typically on the order of at least a magnitude. During operation, the feed gas, which in this case is a slip stream of the syngas, is fed into one or more vessels or adsorption zones in which the syngas components other than hydrogen (along with a minor amount of hydrogen) are adsorbed by the adsorbent. When the adsorbent has achieved capacity, the feed flow into the vessel is shut off, the pressure reduced and the absorbed non-hydrogen components of the syngas are desorbed and removed as a purge gas. If desired, some hydrogen can be used to sweep the vessel at the end of the desorption cycle. The vessel is repressurized and placed back on stream for the next adsorption cycle. Thus, the purge gas contains the CO and any other non-hydrogen syngas components, along with a minor amount of hydrogen. This purge gas is the adsorption offgas which may be sent to disposal or burned as fuel, but which is preferably recycled back into one or more HCS reactors as part of the feed to utilize the valuable CO for the hydrocarbon synthesis. The hydrogen separated from the syngas during the adsorption is typically 99% pure and even purer than 99%. A typical PSA unit has at least one vessel on adsorption, while at least one other vessel is being depressurized and purged, with yet at least one other vessel being repressurized. In membrane separation, bundles of hollow fibers are present in the vessel and the syngas is passed into the vessel in which it flows over the outside of the fibers and out of the vessel. A hydrogen rich permeate gas forms inside each fiber and is removed as a separate, permeate stream. In a typical installation a plurality of such vessels are connected in series, with the permeate from each vessel being the feed into the next successive vessel. High capacity is achieved by using parallel sets of series units. The hydrogen is typically not as pure as that achieved with PSA, but is generally at least about 80% pure. The non-permeate effluents are combined as a CO rich offgas which is utilized in the same manner as for that recovered from the PSA separation. Yet another embodiment of physical separation comprises a combination of PSA or TSA adsorption-desorption and membrane separation. In a typical separation process of this type, the syngas is first passed through a membrane unit to produce a hydrogen-rich gas stream as the permeate. This hydrogen-rich permeate is then passed through a PSA or TSA unit to produce the high purity hydrogen stream and a CO-rich offgas stream. With this process, the amount of offgas produced is less than that obtained using either method by itself.

When using a water gas shift reaction to produce hydrogen, a portion or slip stream of syngas is passed into a water gas shift reactor in which the CO reacts with water vapor in the presence of a shift catalyst, such as nickel on a refractory metal oxide support, at reaction conditions effective to form a mixture of $H_2$ and $CO_2$ which exits the shift reactor, along with the other syngas components, including unreacted CO. If desired, the $CO_2$ may be removed from the shift reactor effluent by means well known to those skilled in the art, such as amine scrubbing. A commercially available process which employs hindered amine scrubbing for $CO_2$ removal is Exxon's Flexsorb® process. The hydrogen rich shift reactor effluent, with or without $CO_2$ removal and, after cooling and drum separation for removal of any excess water, is passed through physical separation means for separating the hydrogen from the CO and other non-hydrogen components present in the gas, to form a relatively pure stream of hydrogen and a CO containing offgas. These gas streams are then utilized in the same manner as above, but with the CO containing offgas typically burned as fuel due to the lower CO content of the offgas. Whether or not a shift reactor is employed depends on the amount of hydrogen desired and the capacity of the syngas generator to satisfy the syngas requirements for both the hydrocarbon synthesis and the hydrogen production.

At least a portion of the hydrocarbons produced by an HCS process according to the invention are typically upgraded to more valuable products, by subjecting all or a portion of the $C_{5+}$ hydrocarbons to conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like. Illustrative, but non-limiting examples of hydroconversion processes useful in the practice of the invention are disclosed in U.S. Pat. Nos. 4,832,819; 4,943,672; 5,059,299; 5,378,348 and 5,457,253.

Referring to FIG. 1, a gas conversion plant 10 comprises an FBSG syngas generating unit 12, a slurry HCS reactor 14, a means 16 for producing hydrogen from syngas, and with box 18 comprising a hydroconversion unit 18. Natural gas, oxygen and steam are fed into the FBSG unit via lines 20, 22 and 24, respectively, to generate syngas comprising a mixture of $H_2$ and CO. Based on 100 moles per hour of CO entering the slurry HCS reactor 14, the syngas stream passed from the syngas generator 12 into line 26 comprises 218 moles per hour of hydrogen and 104 moles per hour of CO, with an $H_2$ to CO mole ratio of about 2.1:1. A commercial scale plant will be much larger, processing as much as 100,000 or moles per hour of CO. Hereinafter, all numbers will refer to moles per hour unless otherwise indicated. Of this, 209 moles of hydrogen and 100 of CO are passed into the HCS reactor 14 via line 26. The HCS reactor contains a catalyst comprising a supported catalytic cobalt component and is designed to operate at 80% conversion of the CO. A syngas slip stream containing 9 moles of hydrogen and 4 of CO is withdrawn from line 26, via line 28, and passed into the hydrogen producing unit 16. In the embodiment in which a PSA unit is used, typically a stream of at least 99% hydrogen is produced, with the remainder being low molecular weight hydrocarbons and nitrogen. For the purpose of this example, 85% of the hydrogen is separated from the slip stream using molecular sieves for the adsorption separation. Eight moles of hydrogen are passed into line 30, with the $H_2$ depleted and CO rich offgas produced by the hydrogen separation withdrawn via line 34 comprising 1 mole of hydrogen and 4 moles of CO. In this embodiment, the offgas is then used as a low BTU value fuel gas. In one embodiment, this CO rich offgas is passed via line 35 into the HCS reactor via line 26, to provide additional CO for the HC reaction. Of the 8 moles of hydrogen leaving the PSA unit, 5 moles are sent into the hydroconversion unit via line 30 to provide the hydrogen for the hydroisomerization of the 700° F.+ fraction of the synthesized hydrocarbons, with 3 moles passed to the HCS catalyst rejuvenation means (not shown) via line 32, for HCS catalyst rejuvenation. The HCS catalyst may be rejuvenated continuously or intermittently either in-situ in the HCS reactor or ex-situ in an external vessel as is known. The hydrocarbons produced in the HCS reactor are removed via line 36 and passed into a hydroconversion unit 18 in which they are fed, along with hydrogen, into a hydroisomerization reactor (shown as 44 in FIG. 2) to produce lower boiling material and in which the heavy, 700° F.+ hydrocarbons are converted into 700° F.− hydrocarbons. The hydrocarbons are hydroisomerized by reacting with $H_2$ in the presence of a suitable hydroisomerization catalyst, such as a cobalt-molybdenum catalyst on a silica-alumina support, at a 700° F+ fraction conversion of 50 wt. %. This means that with each pass through the reactor, 50 wt. % of the 700° F.+ material is converted into 700° F− material having a boiling point of less than 700° F. The hydroisomerized, 700° F.− material is then processed into product fractions or used as a more transportable material for further upgrading operations. Any unconverted 700° F+ material is recycled and mixed with fresh feed to the hydroisomerization reactor. Alternately, the pour point and viscosity of the synthesized liquids withdrawn from the HCS reactor may be reduced via hydroisomerization to make a syncrude or more pumpable and transportable material.

Figure 2:
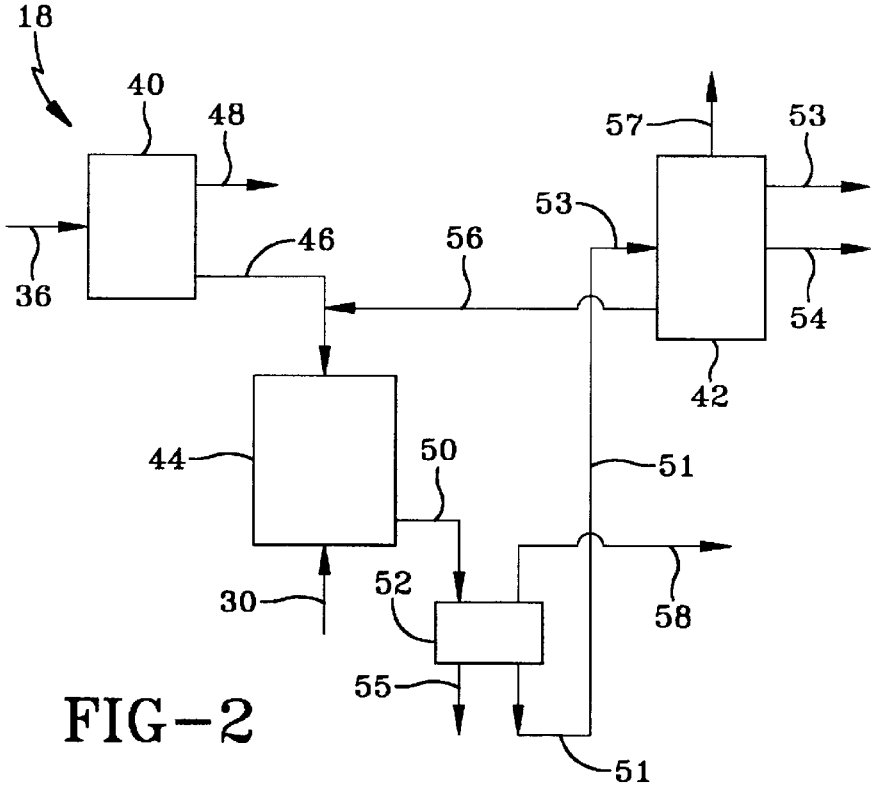
FIG. 2 provides more detail of the hydroconversion.

FIG. 2 illustrates the hydroisomerization unit 18 in greater detail. Referring to FIG. 2, hydroisomerization unit 18 comprises fractionators 40 and 42, and hydroisomerization reactor 44. The liquid hydrocarbon products withdrawn from the HCS reactor are combined with hydrocarbon liquids condensed from the HCS reactor overheads (roughly $C_{11+}$) and passed, via line 36, into fractionator 40 which fractionates the feed into a heavier fraction which is removed via line 46, and a lighter fraction withdrawn via line 48. The heavier fraction, which includes 700° F.+ material withdrawn via line 46, is passed into a hydroisomerization reactor 44 in which it contacts and reacts with the hydrogen produced from the syngas which is passed into the reactor via line 30, in the presence of a suitable hydroisomerization catalyst as set forth above. The hydroisomerized hydrocarbons, which include a 700° F.+ fraction, along with gas comprising mostly unreacted hydrogen, hydrocarbon gasses and water, are withdrawn from reactor 44 via line 50 and passed, following cooling (not shown) and gas and liquid separation in a knock-out drum 52, in which the hydrocarbon liquids and the water are separated from each other and from the unreacted hydrogen and minor amounts of unreacted methane, $C_{2+}$ hydrocarbon gasses and nitrogen. The water is removed via line 55 and the hydrogen-rich tail gas removed via line 58. The hydroisomerized hydrocarbons are removed via line 51 and passed into fractionator 42. Fractionator 42 produces a naphtha and a diesel fraction which are respectively removed via lines 53 and 54, with the remaining 700° F.+ material removed as bottoms via line 56 and recycled back into the hydroisomerization reactor 44, along with fresh feed from fractionator 40. A minor amount of light hydrocarbon gas is removed as overhead via line 57. The unit is designed to accomplish 100% extinction of hydrocarbons boiling higher than 700° F. Typical hydroisomerization reactor conditions include an LHSV of about 1.3, 800–900 psia and a temperature of about 700–750° F. In this particular illustration, the ratio of recycle to fresh feed on a volumetric basis is about 0.5. Under these conditions, of the 5 moles of hydrogen fed into hydroisomerization reactor, 4 moles react with the hydrocarbons in the reactor. The unreacted 1 mole of hydrogen is removed from the reactor as tail gas via line 59.

Figure 3:
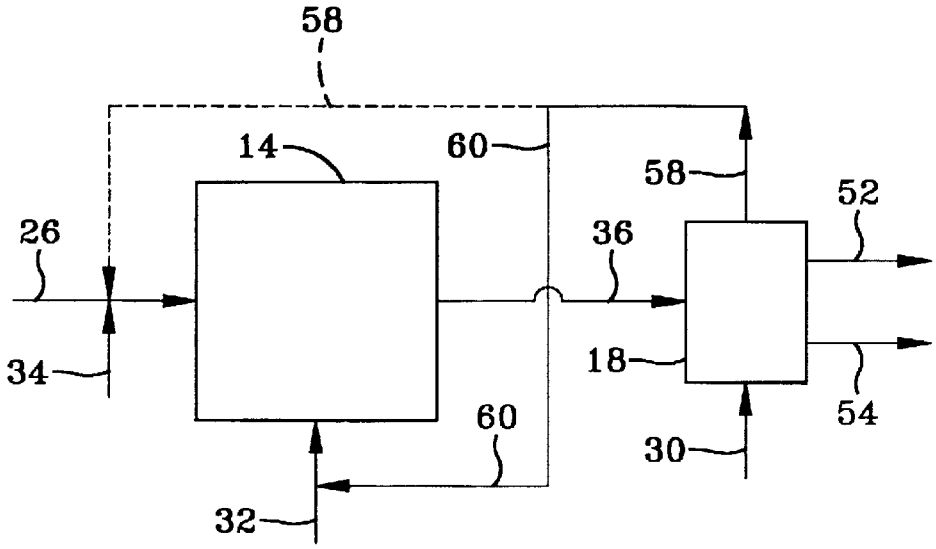
FIG. 3 illustrates an embodiment in which CO rich offgas from the hydrogen production is fed into the HCS reactor and hydrogen rich hydroconversion tail gas is also used for rejuvenation.

FIG. 3 illustrates further embodiments of the process of the invention of FIG. 1. In FIG. 3, the 1 mole of unreacted hydrogen removed from the hydroisomerization reactor as tail gas is passed back into the HCS unit 14 for catalyst rejuvenation via lines via line 58, 60 and 32 (or into a catalyst rejuvenation vessel external of the HCS reactor) and/or into the reactor via lines 58 and 26 as part of the $H_2$ and CO feed for the HCS reaction. Passing the hydrogen rich hydroisomerization reactor tail gas back into the HCS reactor as part of the feed slightly reduces both the syngas generation requirements and the $H_2$ to CO mole ratio of the syngas exiting the syngas generator. In the embodiment in which this tail gas is used for catalyst rejuvenation, the hydrogen production requirements are reduced by the amount of the hydrogen in the tail gas. In a still further embodiment (not shown) in which the hydroisomerization tail gas is recycled back into the hydrogen producing unit 16 in FIG. 1, the relatively high purity of the hydrogen in the tail gas raises the purity of the gas stream fed to the PSA unit and slightly lowers the amount of hydrogen required from the syngas production. Referring again to FIG. 3, the CO rich PSA offgas produced by the hydrogen separation from the syngas slip stream in the process scheme of FIG. 1 is passed into the HCS reaction zone, via line 34, as part of the syngas feed, instead of being consumed as fuel. In this embodiment, all of the HCS feed compositions and rates are the same as in the embodiment illustrated by FIG. 1, except that the portion of the HCS feed from the syngas generator output comprises 207 moles of hydrogen and 96 moles of CO, with the additional 4 moles needed to reach the 100 moles of CO being provided by the PSA offgas passed into the HCS feed line 26 via offgas line 34.

Figure 4:
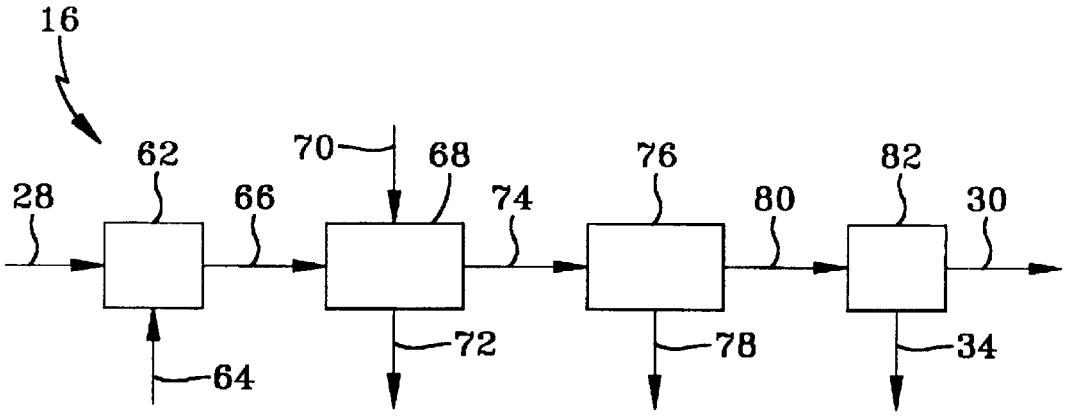
FIG. 4 is a simple block diagram illustrating hydrogen production using a water gas shift reaction and PSA.

FIG. 4 illustrates another embodiment of the invention in which a water gas shift reactor is used to generate more hydrogen from the syngas slip stream, with the shift reactor effluent then passed through physical separation means to separate and recover the hydrogen. Turning to FIG. 4, a hydrogen producing means 16 comprises a water gas shift reactor 62, into which is fed a syngas slip stream via line 28 and, steam via line 64 if the syngas doesn't contain enough water vapor. The shift reactor contains a water gas shift catalyst such as chromium oxide promoted iron oxide. In the shift reactor, the steam reacts with the CO in the presence of the catalyst to form one mole of $H_2$ and one mole of $CO_2$ for each mole of CO and $H_2O$ reacted, to produce a hydrogen rich gas which contains $CO_2$ and any unreacted CO and $H_2O$ which exits the reactor and, after cooling and drum separation for water removal is passed, via line 66 into scrubber 68 for $CO_2$ removal. Scrubber 68 is a conventional contacting tower containing inert packing or fractionation trays. A solvent, such as an aqueous amine solution or an aqueous hindered amine solution such as Flexsorb PS® containing 2-piperidine and ethanolsulfolane for removing the $CO_2$ from the gas, as is disclosed in U.S. Pat. No. 4,112,051, enters via line 70 and removes the $CO_2$. The particular solvent $CO_2$ removal system or other $CO_2$ removal means depends on the extent of $CO_2$ removal desired. If the Flexsorb PS® system is used, virtually all of the $CO_2$ is removed from the gas. The $CO_2$ laden solution is removed via line 72 and sent to solvent recovery, while the scrubbed vapor reduced in $CO_2$ is passed into heat exchanger and separation unit 76, via line 74, in which it is cooled to below 200° F. and the water removed via line 78. The cool gas which still contains water vapor, but not liquid water, is passed into PSA unit 82 via line 80. The PSA unit separates the hydrogen from the rest of the gas to produce 99% or higher purity hydrogen, which is removed via line 30 and used according to any or all of the embodiments above. The offgas resulting from the hydrogen separation is removed via line 34 and is typically used as a low BTU value fuel. Alternately, the $CO_2$ removal system need not be provided, with the purification of the shift effluent accomplished solely through the use of PSA.

While the invention has been described in particular detail for an FBSG syngas generator using processed natural gas as the hydrocarbon feed to the generator, a slurry HCS unit and a hydroisomerization unit for the hydrocarbon conversion, the practice of the invention is not limited to these specific embodiments as those skilled in the art will know and appreciate. Thus, any suitable and convenient source of syngas, feed for the syngas generator and syngas generating process may be used, as may either fluid catalyst bed or fixed catalyst bed, non-slurry HCS processes. Similarly, the conversion process will comprise at least one of those listed above.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A gas conversion process comprising (a) reacting a gaseous hydrocarbonaceous material, oxygen and optionally steam at conditions effective to form a synthesis gas comprising a mixture of $H_2$ and CO, (b) contacting a portion of said synthesis gas with a hydrocarbon synthesis catalyst at reaction conditions effective to react said $H_2$ and CO and form hydrocarbons and reversibly deactivate said catalyst, (c) producing hydrogen from another portion of said synthesis gas, and (d) using the hydrogen for at least one of (i) rejuvenating said catalyst, and (ii) hydroconverting at least a portion of said synthesized hydrocarbons.

2. A process according to claim 1 wherein said hydrogen is produced from said synthesis gas by at least one of (i) physical separation means and (ii) chemical means.

3. A process according to claim 2 wherein said hydrogen is produced from said synthesis gas by means comprising physical separation.

4. A process according to claim 2 wherein said hydrogen production means includes a water gas shift reaction.

5. A process according to claim 3 wherein said hydrocarbon synthesis catalyst comprises a Fischer-Tropsch type of catalyst and wherein at least a portion of said synthesized hydrocarbons are solid at standard room temperature conditions of temperature and pressure.

6. A process according to claim 5 wherein said catalyst comprises a catalytic cobalt component.

7. A process according to claim 6 wherein said hydrocarbon synthesis reaction occurs in a slurry comprising said hydrocarbon synthesis catalyst and bubbles of said $H_2$ and CO in a slurry liquid which comprises said synthesized hydrocarbons which are liquid at said reaction conditions.

8. A process according to claim 7 wherein said hydrogen is used to rejuvenate said catalyst.

9. A process according to claim 3 wherein physically separating said hydrogen from said synthesis gas produces an offgas comprising a CO rich offgas which is used for said hydrocarbon synthesis.

10. A process according to claim 8 wherein physically separating said hydrogen from said synthesis gas produces an offgas comprising a CO rich offgas which is used for said hydrocarbon synthesis.

11. A process according to claim 3 wherein said physical separation comprises passing said synthesis gas through membrane separation means to produce a hydrogen-rich permeate which is passed through pressure swing adsorption means to produce a high purity hydrogen stream.

12. A process according to claim 7 wherein said physical separation comprises passing said synthesis gas through membrane separation means to produce a hydrogen-rich permeate which is passed through pressure swing adsorption means to produce a high purity hydrogen stream.

13. A process according to claim 8 wherein said physical separation comprises passing said synthesis gas through membrane separation means to produce a hydrogen-rich permeate which is passed through pressure swing adsorption means to produce a high purity hydrogen stream.

*14. A process according to claim 7 wherein said synthesized hydrocarbons comprise $C_{5+}$ hydrocarbons.*

*15. A process according to claim 14 wherein at least a part of said $C_{5+}$ hydrocarbons are subjected to conversion.*

*16. A process according to claim 15 wherein said $C_{5+}$ hydrocarbons are subjected to a catalytic process in which the molecular structure of a least a portion of said hydrocarbon is changed.*

*17. A process according to claim 15 wherein said $C_{5+}$ hydrocarbons are subjected to a non-catalytic process in which the molecular structure of at least a portion of said hydrocarbon is changed.*

*18. A process according to claim 16 wherein a diesel fuel is the product of said catalytic processes.*

* * * * *